US 7,819,815 B2

(12) United States Patent
Younes

(10) Patent No.: US 7,819,815 B2
(45) Date of Patent: Oct. 26, 2010

(54) SYNCHRONY BETWEEN END OF VENTILATOR CYCLES AND END OF PATIENT EFFORTS DURING ASSISTED VENTILATION

(75) Inventor: Magdy Younes, Toronto (CA)

(73) Assignee: YRT Limited, Toronto, Ontario (CA)

( * ) Notice: Subject to any disclaimer, the term of this patent is extended or adjusted under 35 U.S.C. 154(b) by 1113 days.

(21) Appl. No.: 10/548,641

(22) PCT Filed: Mar. 15, 2004

(86) PCT No.: PCT/CA2004/000382

§ 371 (c)(1),
(2), (4) Date: Aug. 9, 2006

(87) PCT Pub. No.: WO2004/080516

PCT Pub. Date: Sep. 23, 2004

(65) Prior Publication Data

US 2006/0278223 A1  Dec. 14, 2006

Related U.S. Application Data

(60) Provisional application No. 60/454,533, filed on Mar. 14, 2003.

(51) Int. Cl.
 *A61B 5/08* (2006.01)
(52) U.S. Cl. .................. 600/529; 600/536; 600/538
(58) Field of Classification Search ................ 600/529, 600/536, 538; 128/204.18–204.26
See application file for complete search history.

(56) References Cited

U.S. PATENT DOCUMENTS 6,439,229 B1 *  8/2002  Du et al. ................ 128/204.23

* cited by examiner

*Primary Examiner*—Charles A Marmor, II
*Assistant Examiner*—Michael D'Angelo
(74) *Attorney, Agent, or Firm*—Michael I. Stewart; Sim & McBurney

(57) ABSTRACT

Automatic ongoing adjustment of the cycling-off time of ventilator inflation phase during assisted ventilation in accordance with true respiratory rate of a patient. Electrical signals are generated corresponding to the gas flow exchanged between patient and ventilator (flow) and/or to airway pressure ($P_{aw}$) and the true respiratory rate of the patient (patient RR) is determined on an ongoing basis from the flow and/or $P_{aw}$. The current average cycle duration of patient respiratory efforts (current patient $T_{TOT}$) is estimated from patient RR. A current desirable duration of the inhalation phase (desirable $T_I$) is calculated from the product of current patient $T_{TOT}$ a $T_I/T_{TOT}$ ratio chosen to be in the physiological range, usually 0.25 to 0.50. The ventilator phase is caused to terminate in accordance with the desirable $T_I$.

39 Claims, 13 Drawing Sheets

SYNCHRONY BETWEEN END OF VENTILATOR CYCLES AND END OF PATIENT EFFORTS DURING ASSISTED VENTILATION

REFERENCE TO RELATED APPLICATIONS

This application is a US National Phase filing under 35 USC 371 of PCT/CA2004/000382 filed Mar. 15, 2004 which claims priority under 35 USC 119(e) from U.S. Provisional Patent Application No. 60/454,533 filed Mar. 14, 2003 and under 35 USC 120 from PCT/CA03/00976 filed Jun. 27, 2003.

BACKGROUND TO THE INVENTION

In assisted ventilation, ventilator cycles are triggered by patient inspiratory efforts. There is no mechanism, however, to insure that ventilator cycles terminate at, or near, the end of inspiratory effort. Because the duration of patient inspiratory efforts (neural $T_I$) varies over a wide range (0.5 to 2.5 seconds), the lack of a link between end of ventilator and patient inspiratory cycles often results in ventilator cycles extending well beyond the inspiratory effort (delayed cycling off) or terminating before the end of inspiratory effort, forcing exhalation when the patient is still trying to inhale. The delayed cycling off in particular is often severe with the ventilator cycle extending throughout the patient's expiratory phase (FIG. 1). Because such delayed cycling off interferes with lung emptying during the patient's expiratory phase, the next breath usually begins before lung volume has returned to the neutral level. This delays ventilator triggering and often causes many patient cycles to be ineffective in triggering the ventilator (ineffective efforts, FIG. 1).

Non-synchrony between patient and ventilator is extremely common. Leung et al found that, on average, 28% of patient's efforts are ineffective (Leung P, Jubran A, Tobin M J (1997), Comparison of assisted ventilator modes on triggering, patient effort, and dyspnea. Am J Respir Crit Care Med 155:1940-1948). Considering that ineffective efforts are the extreme manifestation of non-synchrony, less severe, yet substantial, delays must occur even more frequently. Non-synchrony is believed to cause distress, leading to excessive sedation and sleep disruption, as well as errors is clinical assessment of patients since the respiratory rate of the ventilator can be quite different from that of the patient (e.g. FIG. 1).

Cycling-off errors result from the fact that, except with Proportional Assist Ventilation, current ventilator modes do not include any provision that links the end of ventilator cycle to end of patient's inspiratory effort. In the most common form of assisted ventilation, volume-cycled ventilation, the user sets the duration of the inflation cycle without knowledge of the duration of patient's inspiratory effort. Thus, any agreement between the ends of ventilator and patient inspiratory phases is coincidental. With the second most common form, pressure support ventilation, the inflation phase ends when inspiratory flow decreases below a specified value. Although the time at which this threshold is reached is, to some extent, related to patient effort, it is to the largest extent related to the values of passive resistance and elastance of the patient. In patients in whom the product [resistance/elastance], otherwise known as respiratory time constant, is high, the ventilator cycle may extend well beyond patient effort, while in those with a low time constant the cycle may end before the end of patient's effort (Younes M (1993) Patient-ventilator interaction with pressure-assisted modalities of ventilatory support. Seminars in Respiratory Medicine 14:299-322; Yamada Y, Du H L (2000) Analysis of the mechanisms of expiratory asynchrony in pressure support ventilation: a mathematical approach. J Appl Physiol 88:2143-2150). The present invention concerns methods and devices to insure that the end of the ventilator cycle does not deviate substantially from the end of patient's effort. This is achieved by insuring that the duration of the ventilator's inflation phase is a physiologic fraction (0.25-0.50) of the patient's respiratory cycle duration (patient $T_{TOT}$). In this fashion enough time is available for lung emptying during the patient's expiratory phase. By extension, this also reduces dynamic hyperinflation at the onset of patient efforts, thereby also minimizing trigger delays and further improving synchrony.

In PCT/CA03/00976, filed Jun. 27, 2003, (WO 2004/002561), from which this application claims priority, I described an approach to generate a semi-quantitative estimate of the pressure waveform generated by the patient's respiratory muscles. This waveform can be used to identify the onset and end of patient's efforts. According to the aforementioned invention, the end of patient's inspiratory effort, detected by said invention, can be used to cycle off the ventilator, thereby insuring synchrony between the ends of ventilator and patient's inspiratory phases. There is, however, one potential complication to this approach. At times, end of patient effort occurs soon after ventilator triggering. This is because inspiratory muscle activity can be inhibited if inspiratory flow is high, and the ventilator frequently delivers excessive flow soon after triggering. Thus, this approach may result in medically unacceptable inflation times. It was recommended that a back-up procedure be included to insure that the duration of inflation phase is physiologically appropriate. A number of approaches to insure a physiologically appropriate duration of the inflation phase were proposed. These were in part derived from a separate application concerned specifically with methods to synchronize end of ventilator cycle with end of patient effort that do not require knowledge of when said patient efforts end (U.S. provisional Application 60/454,533, Mar. 14, 2003, from which this application claims priority). The current application describes rationale and implementation of said methods in detail and, additionally, introduces other approaches described in the Mar. 14, 2003 U.S. Provisional application (60/454,533) and not referred to in PCT/CA03/00976. The following is the rationale and method for ensuring that the duration of the inflation phase remains within physiologic limits.

In spontaneously breathing subjects and patients, the duration of the inspiratory phase ($T_I$) ranges between 25% and 50% of respiratory cycle duration ($T_{TOT}$). In studies by the inventor using proportional assist ventilation (PAV), with which the duration of the ventilator's inflation phase mirrors the patient's own $T_I$, the ratio of $T_I$ to $T_{TOT}$ ($T_I/T_{TOT}$ ratio) was also found to be between 0.25 and 0.5. Therefore, one approach to insure that the duration of the inflation phase is within the physiologic range is to constrain the duration of the inflation phase to be between 0.25 and 0.50 of the total cycle duration of patient's own efforts (to be distinguished from duration of ventilator cycles). Implementation of this procedure requires knowledge of the true respiratory rate of the patient (as opposed to ventilator rate). The inventor, in association with his students and technicians, described a method for visually determining true patient rate by identifying visually distinctive patterns in the waveforms of respiratory flow and airway pressure (Giannouli et al, American Journal of Respiratory and Critical Care Medicine, vol 159, pages 1716-1725, 1999). According to this approach, true patient rate is the sum of ventilator rate, the number of ineffective efforts occurring during the ventilator's exhalation phase (arrows marked "c", FIG. 1) and the number of additional efforts occurring during inflations triggered by an earlier effort (arrows marked "b", FIG. 1). In PCT/CA03/00976 ventilator cycles triggered by patient (arrows "a", FIG. 1) as well as ineffective efforts occurring during exhalation (arrows "b", FIG. 1) are to be automatically detected from the new composite signal generated from the flow, $P_{aw}$ and volume signals. In the present invention, I describe another approach for identifying ineffective efforts. An approach was described in PCT/CA03/00976 to identify additional efforts occurring during the inflation phase (arrows "c", FIG. 1). This approach is retained here with minor modifications.

As indicated in U.S. Provisional application 60/454,533, and also in PCT/CA03/00976, once the true respiratory rate of patient is known, it becomes possible to calculate the real duration of respiratory cycles of the patient ($T_{TOT}$=60/respiratory rate) and determine the range of inflation times consistent with a physiologic $T_I/T_{TOT}$. For example, if patient's rate is 30/min, $T_{TOT}$ is 2.0 seconds and the physiological range for the inflation phase is 0.5-1.0 second reflecting a $T_I/T_{TOT}$ range of 0.25 to 0.50. The desirable duration of the ventilator's inflation phase is then determined by multiplying patient $T_{TOT}$ by a user selected physiologic $T_I/T_{TOT}$ ratio or a suitable default value (e.g. 0.4). The ventilator's inflation phase can then be made to cycle off after said desirable duration.

There are a number of ways by which the duration of the ventilator's inflation phase can be made to correspond to desirable $T_I$. One approach, discussed in U.S. Provisional application 60/454,533 and also proposed in PCT/CA03/00976, is to terminate the inflation phase at the specified desirable duration following onset of inspiratory effort or following the time of ventilator triggering. With this approach ventilator inflation varies strictly with average respiratory rate discerned from a number of elapsed breaths. There is no provision, therefore, for accommodating breath-by-breath changes in duration of inspiratory effort since the desirable duration is predetermined before the effort begins (based on an average result obtained from a number of elapsed breaths). Another approach, particularly suited for pressure support ventilation, is to retain the usual criterion for terminating the inflation phase, namely when inspiratory flow reaches a specified threshold, but flow threshold is adjusted to produce the desired $T_I$. This would permit breath-by-breath changes in patient's $T_I$ to influence ventilator $T_I$ in current breaths but ventilator $T_I$ would, on average, correspond to desirable $T_I$. This general approach was proposed in U.S. Provisional application 60/454,533. In PCT/CA03/00976 I proposed that this general approach be implemented by measuring the flow occurring at the desirable $T_I$ in a number of elapsed breaths. This would then become the flow threshold for terminating the inflation phase in prospective (i.e. current) breaths. An alternative approach proposed in U.S. Provisional application 60/454,533 (but not in PCT/CA03/00976) is to measure actual ventilator $T_I$ in a number of elapsed breaths. This actual value is compared with desirable $T_I$ with the difference (i.e. actual $T_I$–desirable $T_I$) representing an error signal that can be used for closed-loop control of the flow threshold for cycling off, using any of a number of closed-loop control approaches. Alternatively, the error signal can be the difference between actual $T_I/T_{TOT}$ (i.e. actual $T_I$/patient $T_{TOT}$) and desirable $T_I/T_{TOT}$.

In my experience, patient's respiratory rate often changes substantially from time to time. An essential feature of this invention is, therefore, the provision for automatic means to monitor patient respiratory rate and to update the relevant values (e.g. desirable $T_I$, actual $T_I$, $T_I$ error ... etc) at frequent intervals.

With current methods of assisted ventilation tidal volume is directly related to the duration of the inflation phase. Changes in the duration of the inflation phase produced by the methods of the current invention are, therefore, expected to result in corresponding changes in tidal volume. In another aspect of the current invention provision is made to partially or completely offset the resulting changes in tidal volume by concomitantly increasing inspiratory flow (in the case of volume-cycled ventilation) or the support pressure (in the case of pressure support or assist/pressure control ventilation) when the duration of the inflation phase is decreased, and vice versa.

SUMMARY OF INVENTION

In summary, this invention concerns a novel approach for cycling off ventilators in which the duration of the inspiratory phase is constrained to be a physiological fraction (0.25 to 0.50) of the duration of patient breathing cycles (patient $T_{TOT}$). One aspect of the invention is the provision of means for ongoing automatic determination of patient $T_{TOT}$ from the flow and/or airway pressure signals. In another aspect, control of cycling off time in pressure support ventilation is effected by measuring the difference between actual and desirable $T_I$ and using this error signal (difference between actual and desirable $T_I$) to determine the flow threshold for cycling off using closed loop control methods. In still another aspect of the invention, the level of delivered flow or pressure during the inflation phase is altered in concert with changes in ventilator $T_I$ so as to partially or completely offset the changes in tidal volume that would result from uncompensated changes in the duration of the inflation phase.

In accordance with one aspect of the present invention, there is provided a method for automatic ongoing adjustment of the cycling-off time of ventilator inflation phase during assisted ventilation in accordance with true respiratory rate of a patient, comprising generating electrical signal(s) corresponding to rate of gas flow exchanged between patient and ventilator (flow) and/or to airway pressure ($P_{aw}$), determining true respiratory rate of patient (patient RR) on an ongoing basis from the flow and/or $P_{aw}$ signals, estimating current average cycle duration of patient respiratory efforts (current patient $T_{TOT}$) from the patient RR, calculating a current desirable duration of the inhalation phase (desirable $T_I$) from the product of current patient $T_{TOT}$ and a $T_I/T_{TOT}$ ratio chosen to be in the physiological range (usually 0.25 to 0.50) and causing ventilator inflation phase to terminate in accordance with the desirable $T_I$.

In accordance with a further aspect of the present invention, there is provided a device for automatic ongoing adjustment of the cycling-off time of ventilator inflation phase during assisted ventilation in accordance with true respiratory rate of the patient, comprising circuitry for generating electrical signal(s) corresponding to the flow exchanged between patient and ventilator (flow) and/or to airway pressure ($P_{aw}$), digital or analog circuitry means for determining true respiratory rate of patient (patient RR) on an ongoing basis from the flow and/or $P_{aw}$ signals, digital or analog circuitry means for estimating current average cycle duration of patient respiratory efforts (current patient $T_{TOT}$) from the patient RR, digital or analog circuitry means for calculating a current desirable duration of the inhalation phase (desirable $T_I$) from the product of current patient $T_{TOT}$ and a $T_I/T_{TOT}$ ratio chosen to be in the physiological range (usually 0.25 to 0.50), and means to cycle off ventilator inflation phase in accordance with the desirable $T_I$.

DESCRIPTION OF THE PREFERRED EMBODIMENT OF THE INVENTION

Figure 3:
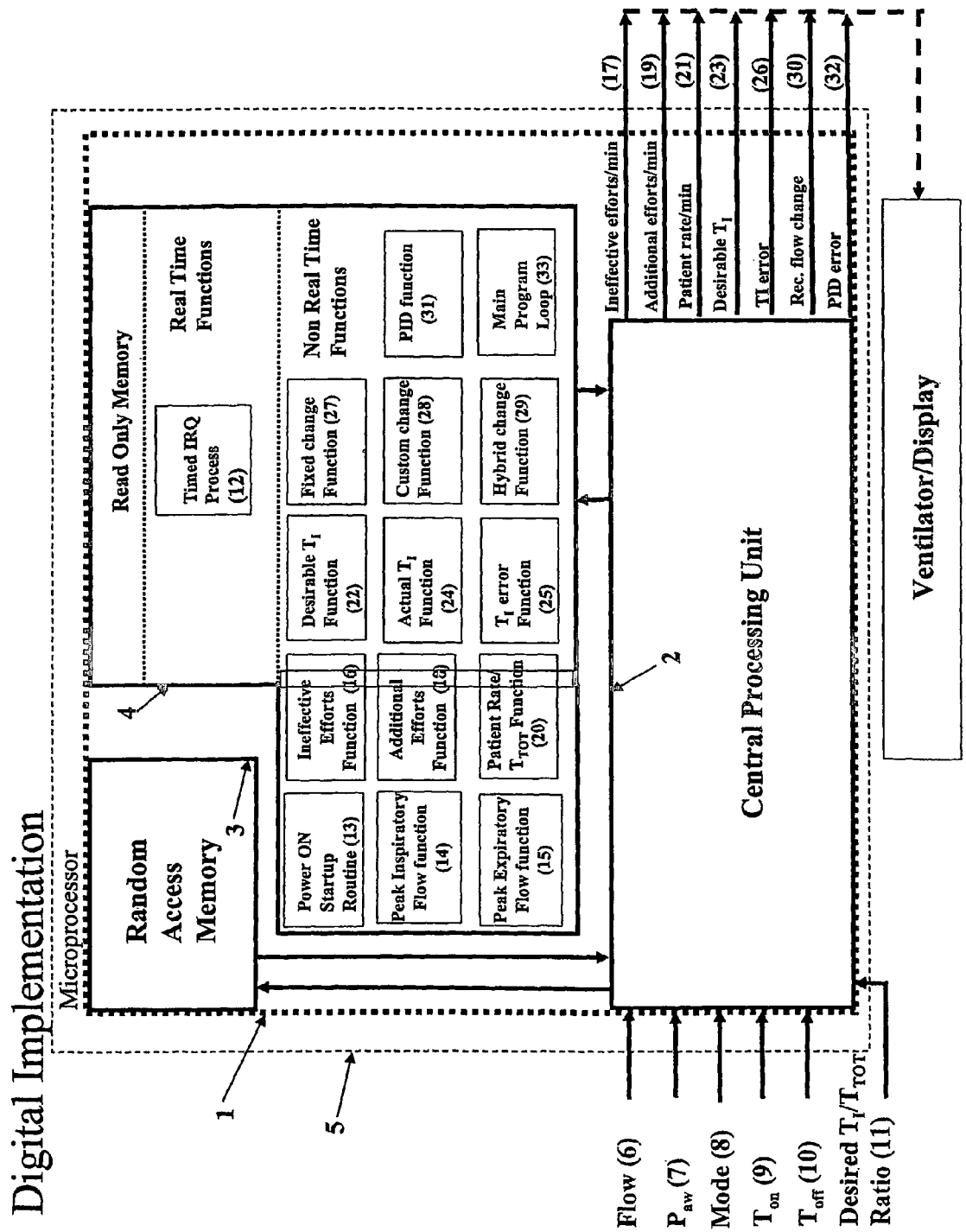
FIG. 3 is a block diagram of the preferred embodiment of digital implementation of the present invention.
Figure 4:
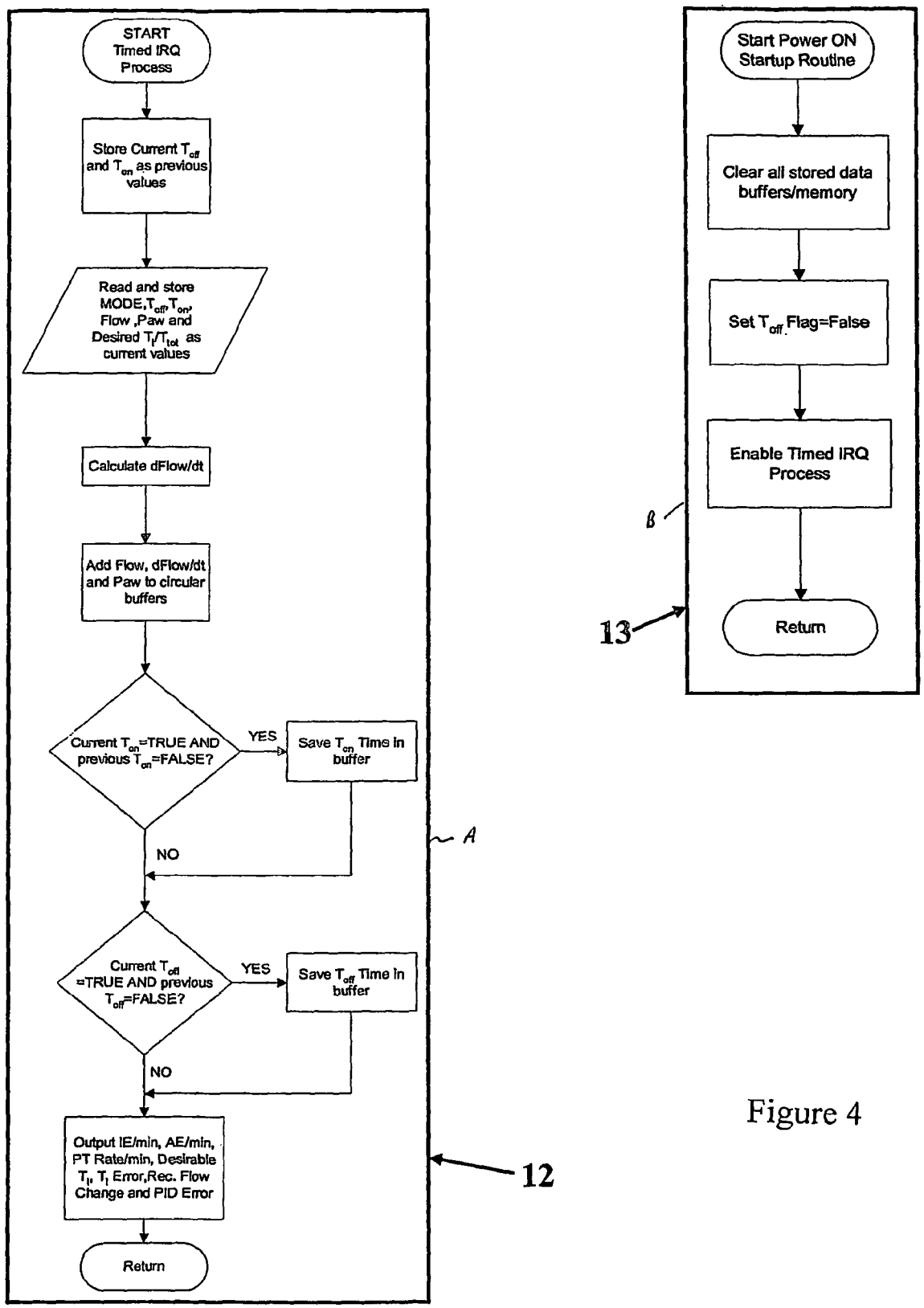
FIGS. 4 to 13 are flow charts of the different functions listed in the block diagram of FIG. 3.
Figure 5:
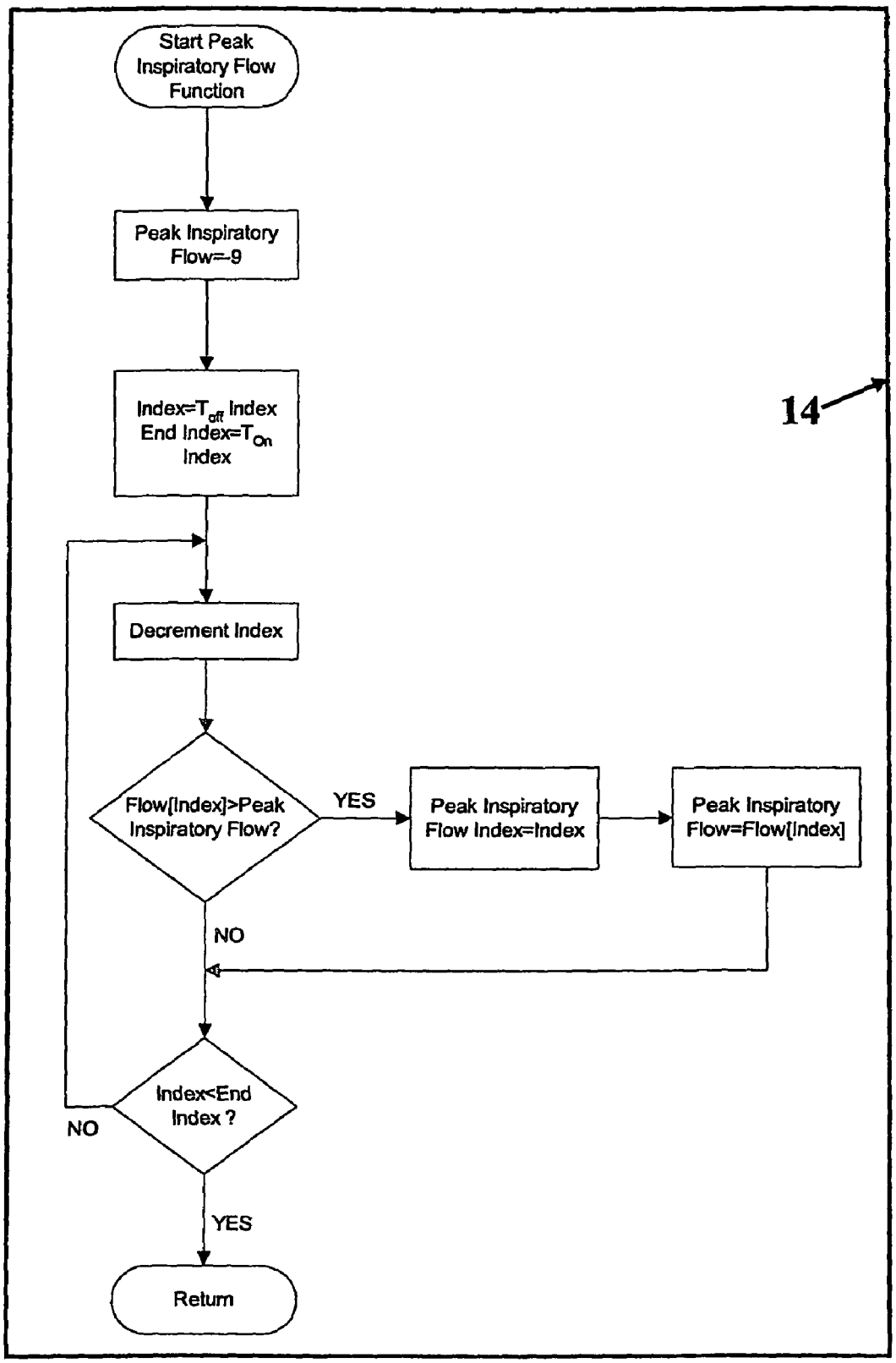
Figure 6:
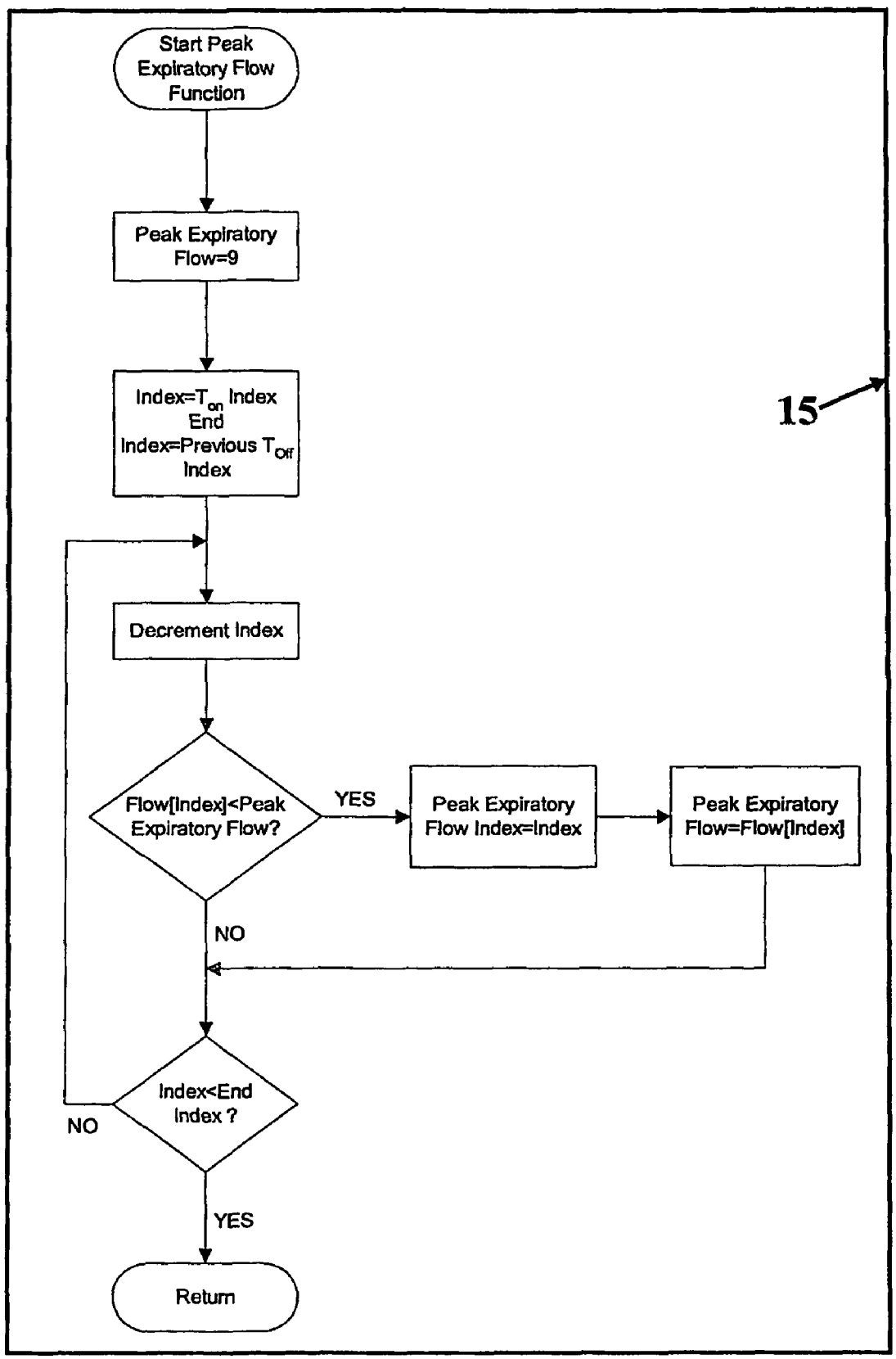
Figure 7:
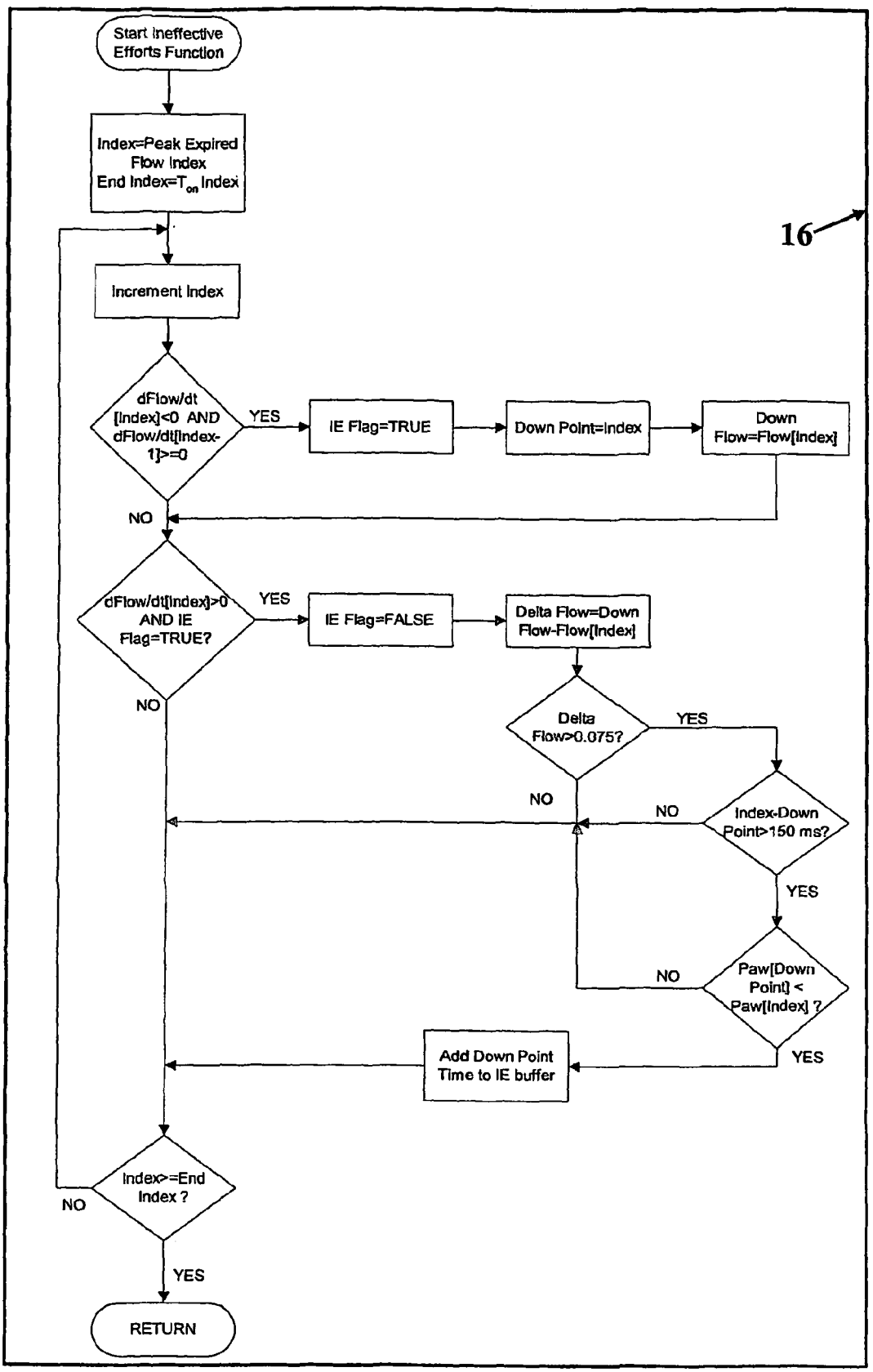
Figure 8:
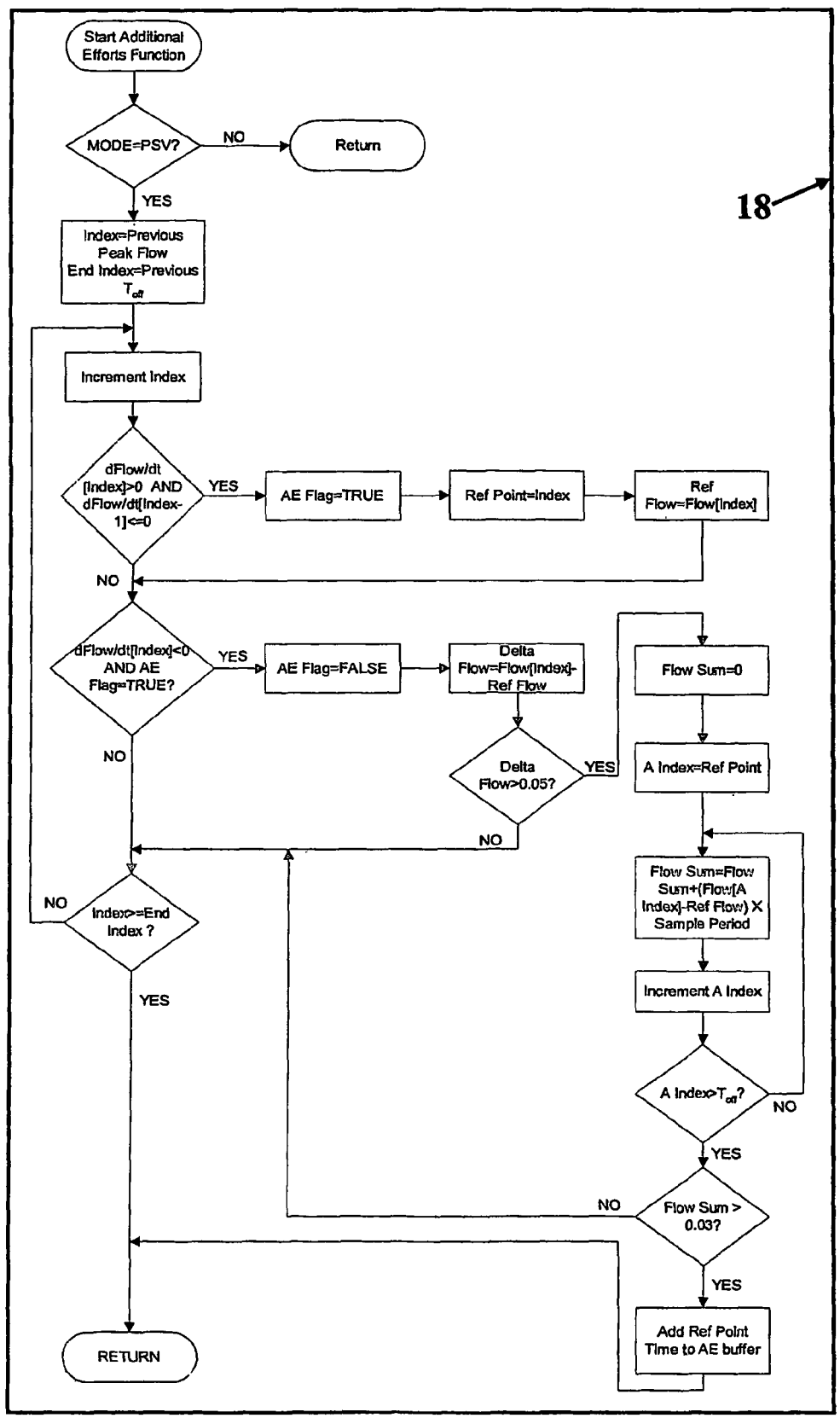
Figure 9:
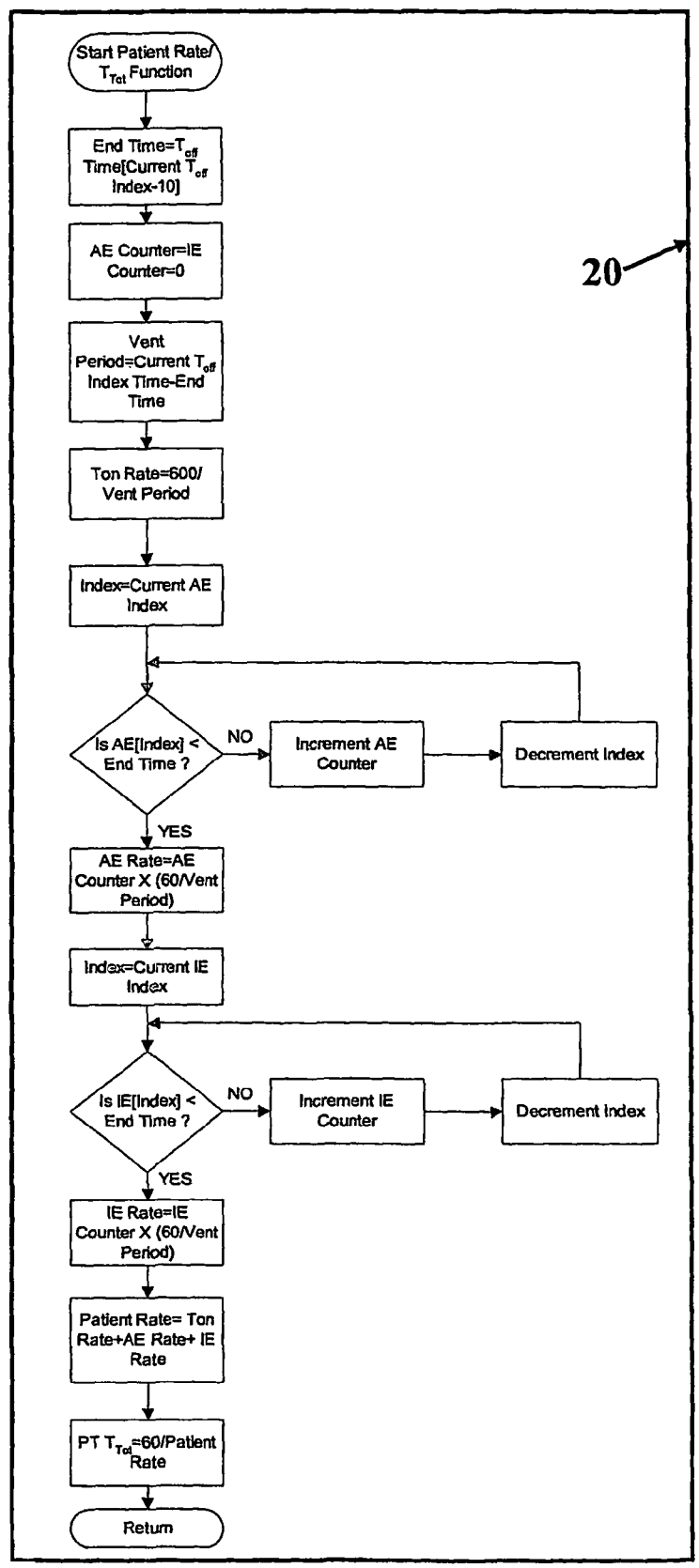
Figure 10:
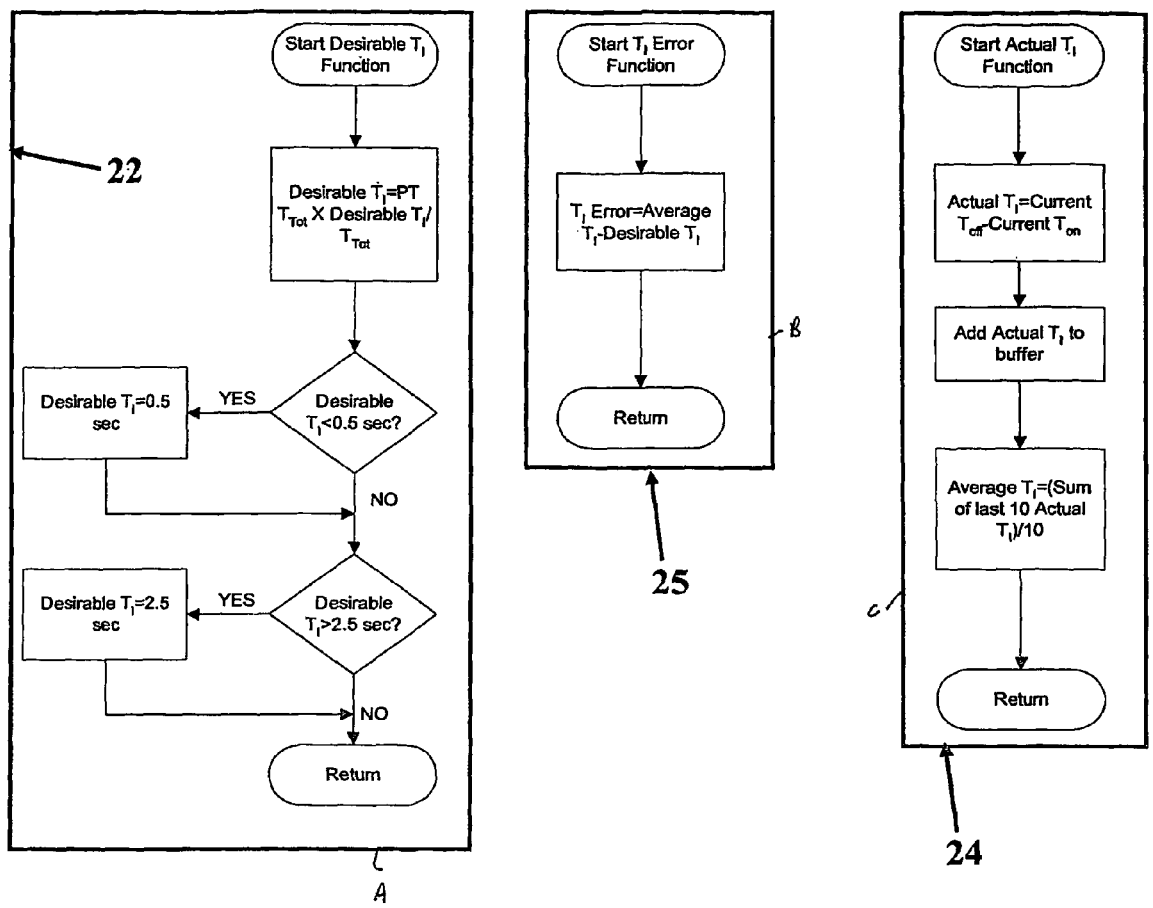
Figure 11:
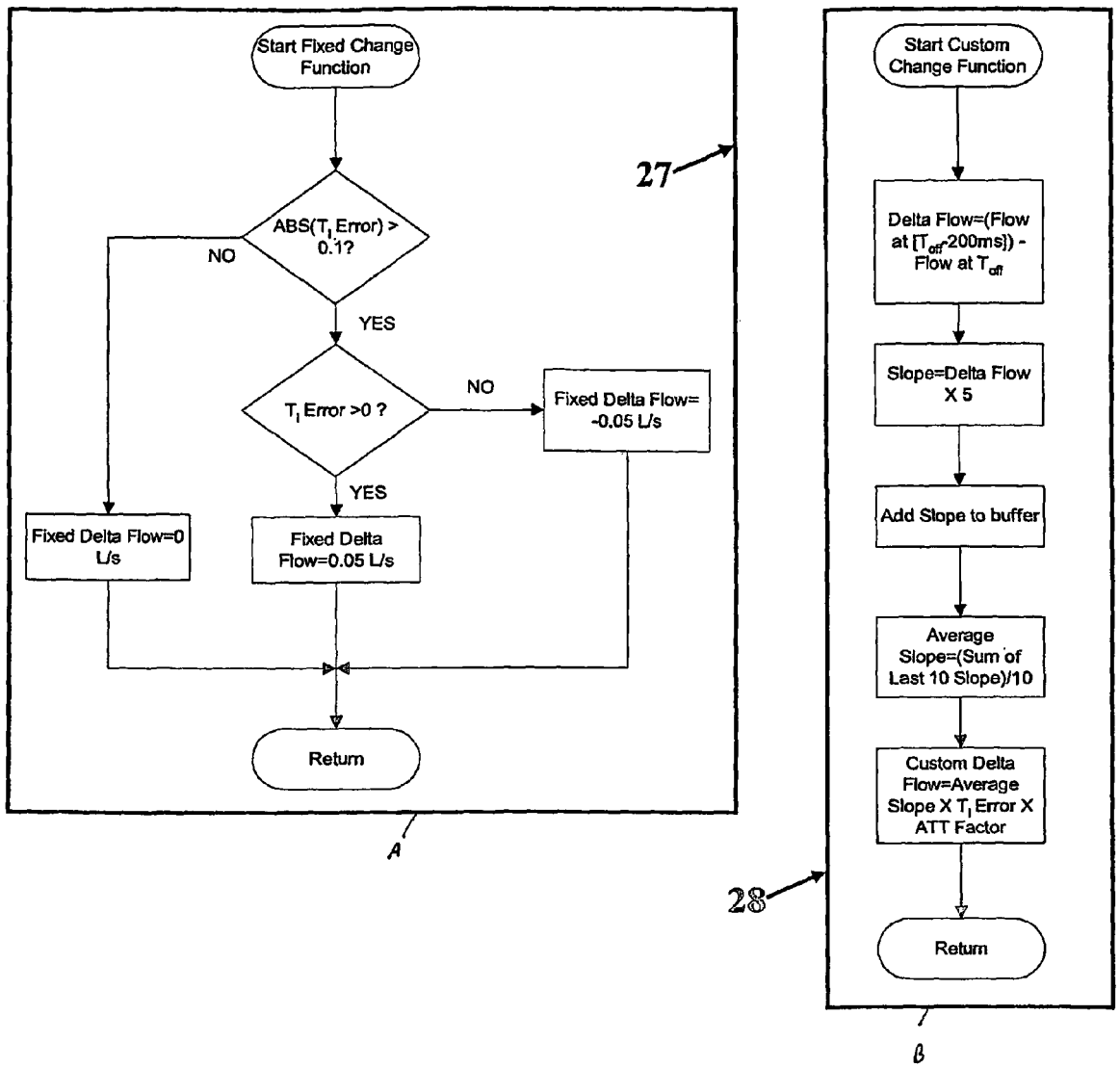
Figure 12:
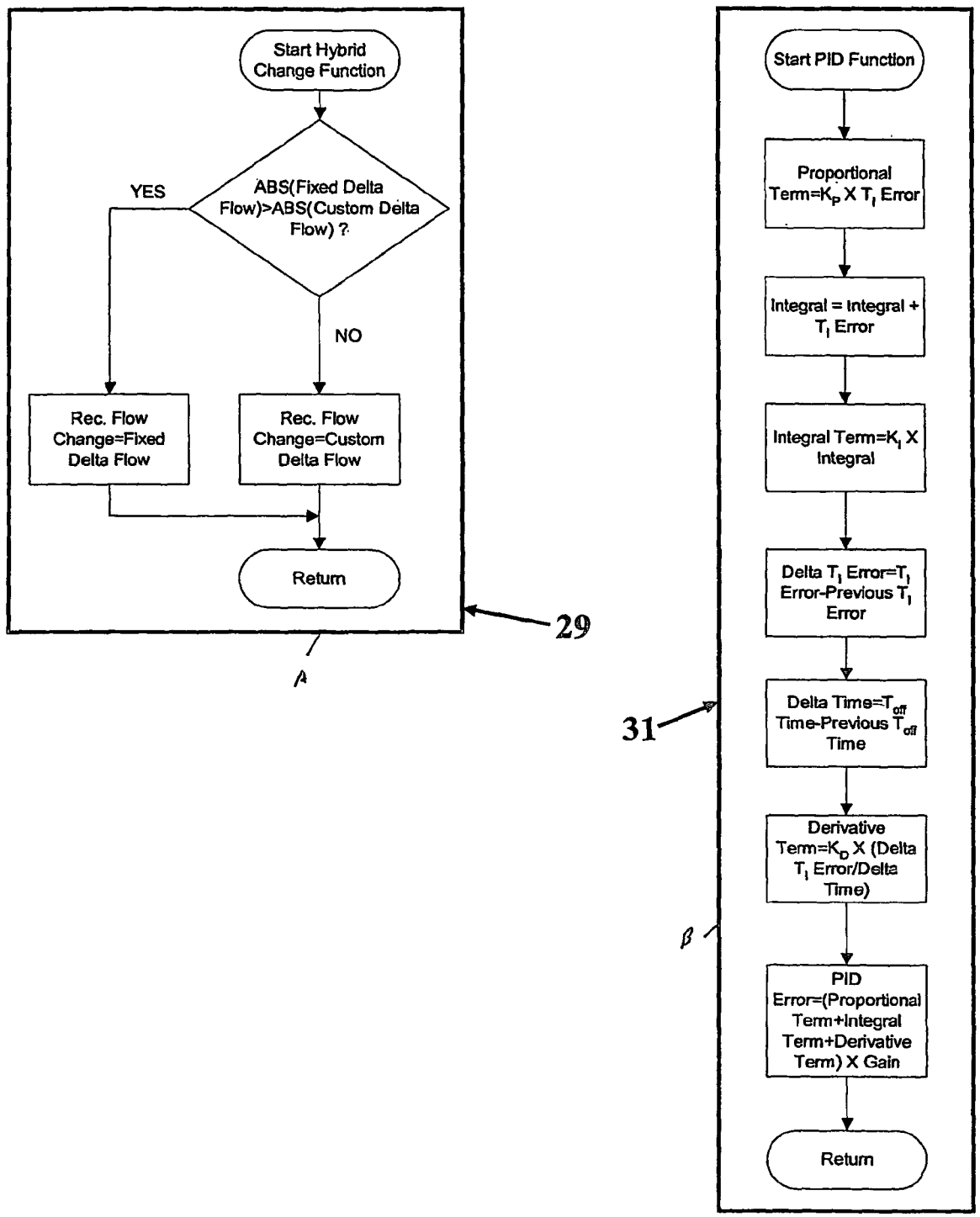
Figure 13:
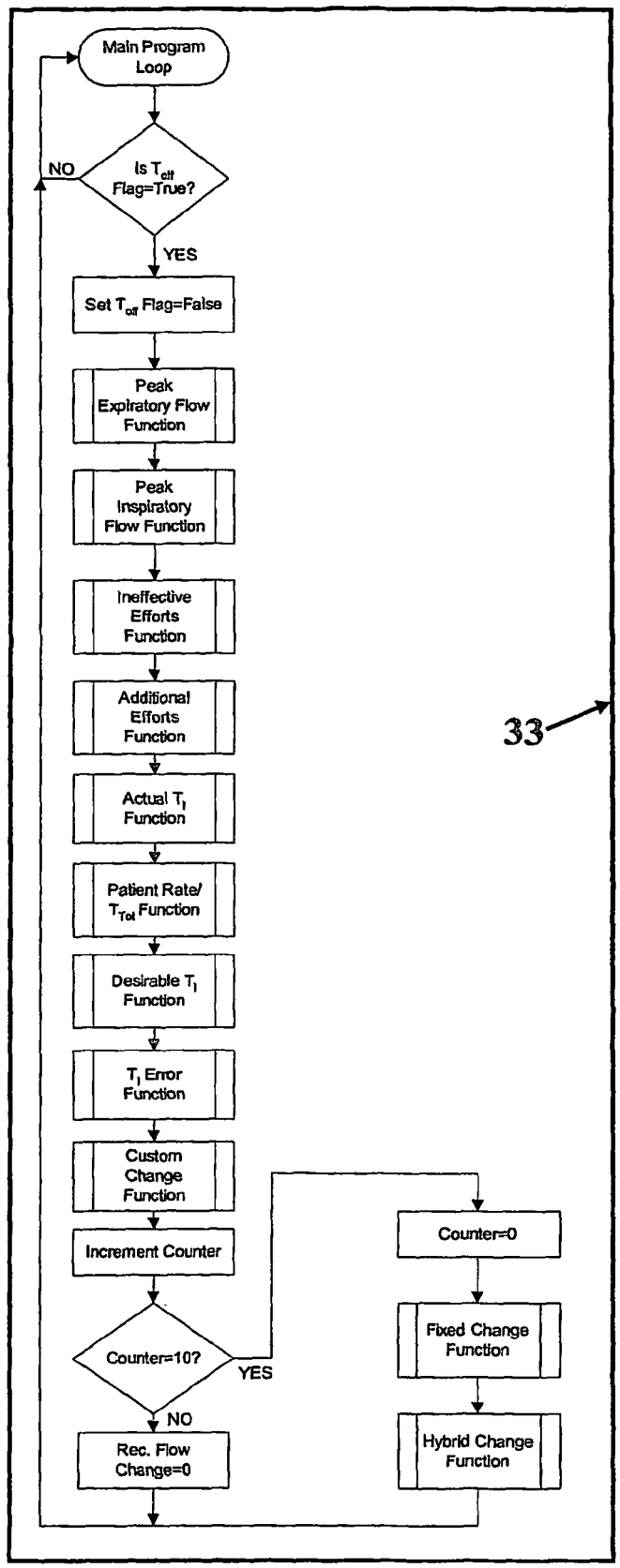

A digital implementation of a preferred embodiment of the invention will be described here (FIG. 3) because the method of the invention is primarily intended for incorporation in microprocessor-based ventilators. As such, the method can be installed in a free-standing microprocessor that interacts with the ventilator's control circuitry or may be fully incorporated in the ventilator's resident computer. It is recognized, however, that most of the functions described here can be implemented using standard analog circuits.

The basic hardware requirements (microprocessor, 1) are a Central Processing Unit (CPU, 2), Random Access Memory (RAM, 3) and Read Only Memory (ROM, 4)).

A. Inputs:

It is assumed here that inputs are in digital form. If some or all are available only in analog form, an analog to digital converter (not shown) must be installed upstream from the CPU to receive and digitize the analog inputs.

Inputs may vary depending on user preference and independent availability, within the host ventilator, of signals required for implementation of the present invention. In the preferred embodiment illustrated in FIG. 3 (5), it is assumed that the device of the present invention will be responsible for determining patient's respiratory rate but that signals corresponding to onset and end of ventilator breaths are already available from the host ventilator. Modifications to this arrangement will be described at the appropriate locations below.

A.1 Inputs Corresponding to Flow (6) and/or Airway Pressure ($P_{aw}$, 7):

Virtually all modern ventilators monitor air flow within the ventilator circuit and generate a signal corresponding to the rate of gas flow exchanged between patient and ventilator. Furthermore, airway pressure ($P_{aw}$) is routinely monitored. These resident signals can be used as inputs to the microprocessor implementing the current invention. Alternatively, if the present invention is incorporated in an external device, flow and $P_{aw}$ signals can be generated independently by standard techniques (for example, as described in PCT/CA03/00976).

Flow (6) and $P_{aw}$ (7) signals are used to determine a) patient's respiratory rate and b) to implement a specific method (custom change function) of closed loop control of "cycling-off" flow threshold in the pressure support mode (see B.2.2.4, below). In the event patient's respiratory rate is determined from only one of these signals (for example, flow only or $P_{aw}$ only) and a different method of closed loop control of "cycling-off" flow threshold is used, the other input can be omitted.

A.2 Mode (8):

The present invention is primarily intended for use when the ventilator is in the pressure support mode (PSV). It can, however, also be used in the assist/control modes (A/C). Because implementation of this invention varies with the mode used (see FUNCTIONS, below), an input reflecting the mode being used is recommended. When the current invention is incorporated within the ventilator, this input can be obtained directly from the ventilator's control system. Alternatively, if the invention is incorporated in an external device (for example, as described in PCT/CA03/00976), the mode of ventilation is entered by the user.

A.3 $T_{on}$ (9):

This is a signal that indicates either the time of onset of patient inspiratory effort or the time of onset of a ventilator inflation cycle depending on which is available. In practice, if the present invention is implemented, dynamic hyperinflation is minimized and there should be little difference between the two times (i.e. trigger delay should be minimal). In all current ventilators, the ventilator control system generates a triggering signal that initiates a ventilator cycle. This signal can be used as $T_{on}$ (9). Ventilator cycles can be triggered either in response to patient effort (patient-triggered cycles) or by the ventilator itself if a triggering effort did not occur within a time specified by a user-selected back-up rate (ventilator-triggered cycles). Ventilators can distinguish between these two types of triggers. If the ventilator's trigger signal is to be used as $T_{on}$, only the signals related to patient-triggered cycles are communicated to the microprocessor implementing the current invention. If the current invention is implemented in an external device (i.e. the ventilator's trigger signals are not available), the onset of ventilator cycle can be identified externally from the pressure and/or flow signal using any of a number of obvious techniques (for example, as described in PCT/CA03/00976).

According to recent developments (PCT/CA03/00976), onset of patient inspiratory effort can be identified non-invasively. Such devices/methods may be incorporated in future ventilators or be used as external devices. In either case, the onset of patient inspiratory effort identified by such device/method, or by other means available to the ventilator, can be used as $T_{on}$ for the sake of the current invention.

A.4 $T_{off}$ (10):

This is a signal that indicates the end of the ventilator's inflation phase. It can be obtained directly from the ventilator's control system (cycling-off signal) or be derived independently from the flow (6) and/or $P_{aw}$ (7) signal using any of a number of obvious methods (for example, as described in PCT/CA03/00976).

A.5 Desired $T_I/T_{TOT}$ Ratio (11):

This ratio is preferably a user-selected input that would normally range between 0.25 and 0.50. Alternatively, it can be replaced by a default value. A default value of 0.4 would be appropriate, but other values preferred by manufacturers may be used instead. One embodiment is to link the default $T_I/T_{TOT}$ to patient respiratory rate with high default ratios being used when patient rate is high, and vice versa. This would preclude having very short $T_I$ when patient rate is very high and very long $T_I$ when rate is slow. A suggested relation is to use a default ratio of 0.5 when rate is 50 min$^{-1}$ and a ratio of 0.3 when rate is 10 min$^{-1}$, with intermediate values for intermediate rates.

B. Functions:

B.1 Real-Time Functions:

The timed interrupt request process (Timed IRQ process, 12) is executed at suitable intervals (for example, every 5 msec). This collects data from various inputs (see FIG. 3 for inputs), calculates the time derivative of flow and stores collected and derived data in memory. This also checks for the times at which $T_{on}$ and $T_{off}$ occur and stores them in memory.

B.2 Non Real-Time Functions:

B.2.1 Power ON Start-Up Routine (13):

The power on start-up routine clears the memory and enables the Interrupt Request (IRQ) Process.

Figure 1:
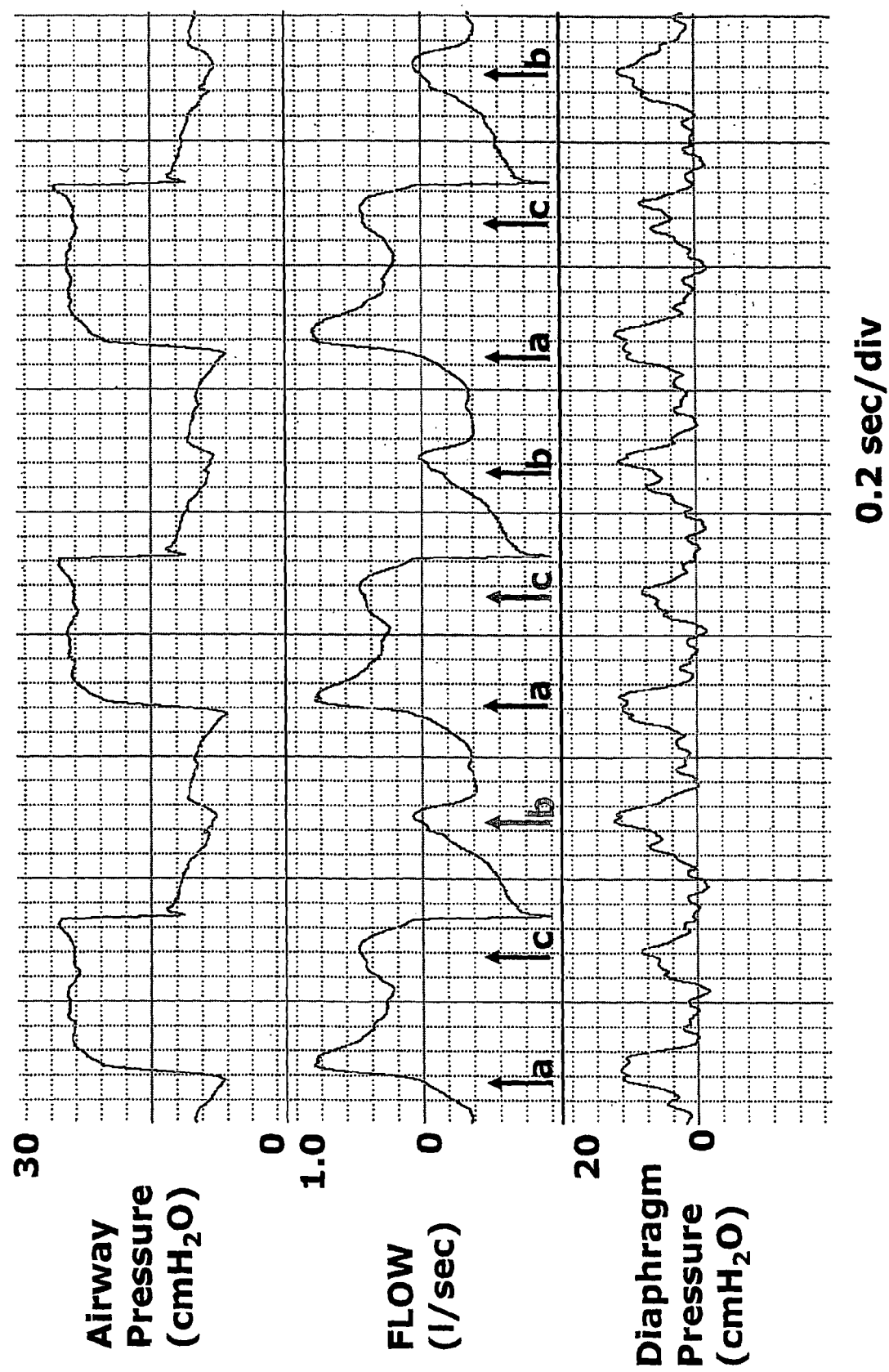
FIG. 1 contains tracings showing flow and airway pressure in a ventilated patient, along with diaphragm pressure to indicate patient's own efforts. Arrows marked "a" denote efforts that triggered ventilator cycles. Arrows marked "b" indicate efforts that occurred in the exhalation phase but failed to trigger the ventilator (ineffective efforts). Arrows marked "c" denote extra efforts that occurred during the same ventilator inflation phase triggered by an earlier effort (additional efforts).

B.2.2 Functions to Determine Patient Respiratory Rate:

As indicated in the Background section above, patient's respiratory rate may be quite different from ventilator's rate (for example, FIG. 1). It is the patient's rate that needs to be known in order to set the ventilator's inflation time to be in the physiological range. Furthermore, since patient's rate may vary considerably from time to time, it is necessary to monitor patient's rate on an ongoing basis. In this preferred embodiment (1), I have developed an automatic continuous digital approach based on the visual (identified by eye) approach described by Giannouli et al (Am. J. Respir. Crit. Care Med. 159: 1716-1725, 1999). This approach is described here only to illustrate that patient rate can be monitored automatically on an ongoing basis using simple processing of universally available signals (flow and/or $P_{aw}$). There are a number of other approaches that can be employed to achieve the same end. For example, a signal combining flow, volume and $P_{aw}$ can be generated from which true respiratory rate can be estimated, as described in PCT/CA03/00976. Alternatively, although such methods have not yet been specifically described, it may be possible to obtain patient's rate by spectral analysis of the flow and/or $P_{aw}$ signal (looking for the frequency of significant power peaks in the respiratory rate range (10 to 50 min$^{-1}$)) or by other mathematical analyses of these signals. Furthermore, it is theoretically possible to estimate patient rate from signals other than flow and/or $P_{aw}$, for example from changes in electrical impedance or inductance of the chest wall, from strain gauges placed on the chest wall, or from monitoring electrical activity of respiratory muscles. Other methods may be developed in the future to estimate patient's rate. The specific way by which patient rate is continuously monitored is not the subject of the current patent application. Where methods other than the one described here are used to continuously monitor patient's rate the result of such determination can be inputted directly in the microprocessor of the present invention.

In the approach used in the preferred embodiment (1), patient's rate is estimated from the sum of a) patient triggered ventilator cycles ("a" arrows, FIG. 1), b) respiratory efforts occurring during the ventilator's exhalation phase that did not trigger ventilator cycles (ineffective efforts, "b" arrows, FIG. 1), and c) additional inspiratory efforts occurring during the ventilator's inflation phase (additional efforts, "c" arrows, FIG. 1). Patient triggered ventilator cycles ($T_{on}$) are identified by the IRQ process (12) and stored in memory. Separate functions are included for detection of ineffective efforts (16) and additional efforts (18). A fourth function (20) sums the 3 results over specified elapsed intervals to obtain patient's rate/minute and average patient cycle duration (patient $T_{TOT}$). Before implementing these functions it is desirable to determine the time of occurrence of peak inspiratory and expiratory flow.

B.2.2.1 Peak Inspiratory Flow Function (14):

This function determines the magnitude and time of occurrence of maximum flow during the inflation phase in each elapsed ventilator cycle. It searches the flow signal between $T_{on}$ and $T_{off}$ of the preceding inflation phase looking for the highest value and stores the actual flow value and its time.

B.2.2.2 Peak Expiratory Flow Function (15):

This function determines the magnitude and time of occurrence of peak expiratory flow during the expiratory phase in each elapsed ventilator cycle. It searches the flow signal between $T_{off}$ and the next $T_{on}$ looking for the lowest value and stores the actual flow value and its time.

Figure 2:
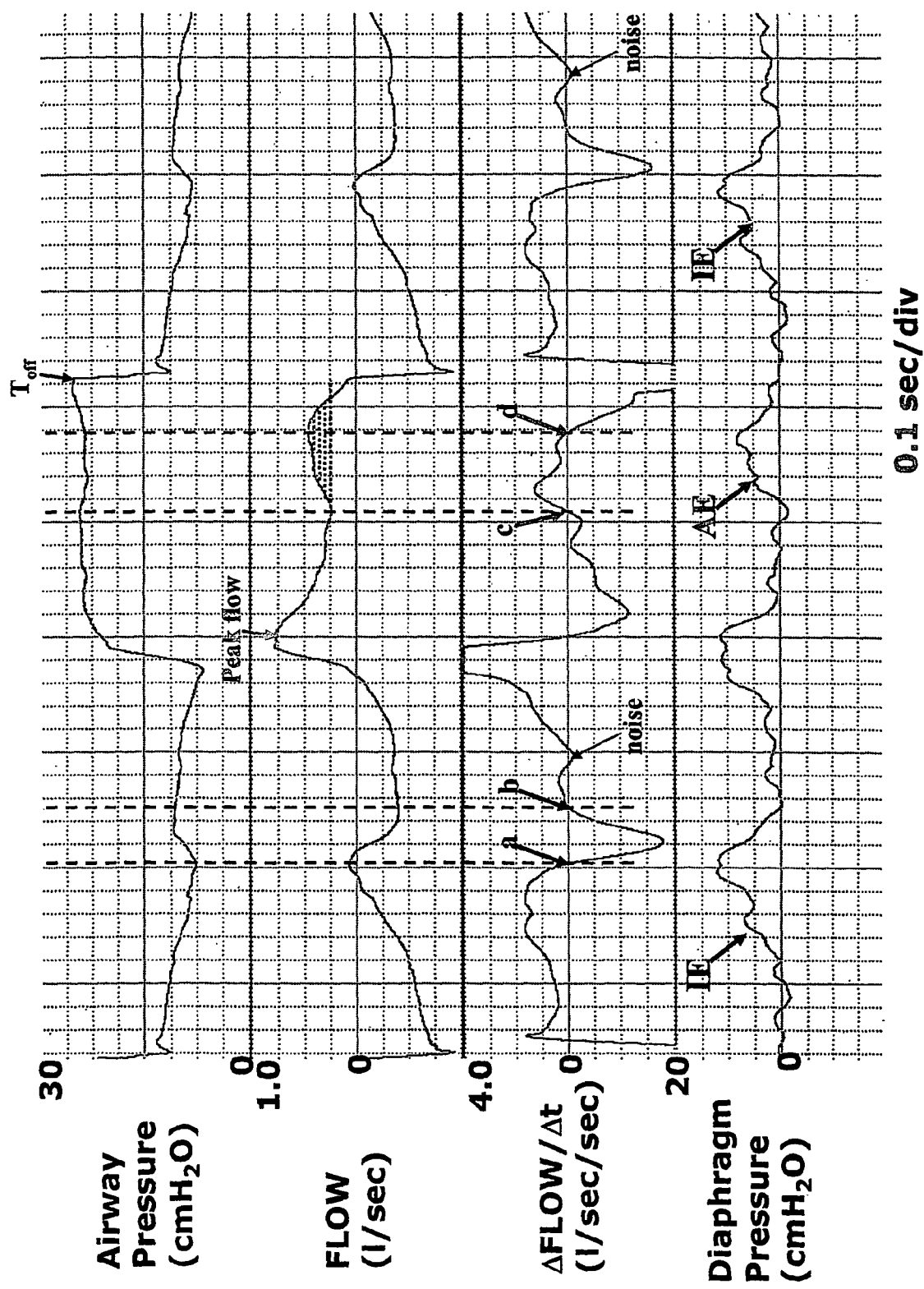
FIG. 2 contains tracings showing a method of detecting ineffective (IE) and additional (AE) efforts from the derivative of the flow signal ($\Delta$flow/$\Delta$t).

B.2.2.3 Ineffective Efforts Function (16):

This function searches the flow signal of each elapsed exhalation phase in the interval between peak expiratory flow (15) and next $T_{on}$ (9) for evidence of efforts that did not trigger a ventilator cycle. FIG. 2 shows the principle of the preferred approach described herein. FIG. 2 shows tracings of airway pressure ($P_{aw}$), flow, rate of change in flow ($\Delta$flow/$\Delta$t) and diaphragm pressure. An ineffective effort occurred at the arrow (arrows marked IE). In the passive state, once expiratory flow reaches its peak value, it should progressively decrease (i.e. flow becomes less negative) until the next ventilator cycle. This should result in a continuously positive $\Delta$flow/$\Delta$t signal. When an inspiratory effort occurs, expiratory flow initially moves toward zero at a faster rate (and flow may become transiently positive, FIG. 2). If the effort ends without triggering the ventilator, as illustrated in FIG. 2 (arrow marked IE), expiratory flow increases again (i.e. flow becomes more negative). After reaching a maximum value, expiratory flow begins decreasing again toward zero and continues to do so until the next inspiratory effort. This sequence results in a characteristic pattern in the $\Delta$flow/$\Delta$t signal. The signal rises at a faster rate than before with the onset of effort. Then the signal declines transiently into the negative range (point "a", FIG. 2) and finally crosses zero again into positive range (point "b", FIG. 2). During passive expiration, $\Delta$flow/$\Delta$t should not become negative except very briefly in association with transient noise, such as secretions or tube vibrations. Such artifactual negative transients have much shorter durations than ineffective efforts (see arrows marked "noise" in FIG. 2). Accordingly, identification of ineffective efforts in this preferred embodiment of the invention is based on detecting negative transients in the $\Delta$flow/$\Delta$t signal having a duration that is greater than that of the usual noise. From experience, I found that a negative transient duration of approximately 0.15 second provides a good separation between noise and ineffective efforts. Two other optional conditions are implemented in the preferred embodiment that, based on experience, minimize false identification of ineffective efforts: a) requiring that flow at the onset of the negative transient in $\Delta$flow/$\Delta$t (point "a", FIG. 2) be higher than flow at the end of the transient (point "b", FIG. 2) by a specified amount. In FIG. 2, the difference in flow between the two points was 0.4 l/second. A minimum difference of 0.075 l/second is recommended. Note that a second negative transient related to noise did not meet this criterion, (b) requiring that $P_{aw}$ at the onset of the negative transient in $\Delta$flow/$\Delta$t point "a", FIG. 2) be lower than $P_{aw}$ at the end of the transient (point "b", FIG. 2). When an ineffective effort is identified, its time is stored in memory. From this, the number of ineffective efforts per minute can be calculated and displayed (17).

During the exhalation phase $P_{aw}$ is a function of expiratory flow and resistance of the exhalation tube/valve combination. Accordingly, changes in flow produce corresponding changes in $P_{aw}$; when expiratory flow decreases (i.e. becomes less negative) $P_{aw}$ also decreases (i.e. becomes less positive) (for example, note that $P_{aw}$ during exhalation is a mirror image of flow, FIG. 2). For this reason, detection of ineffective efforts can be made from the $P_{aw}$ signal using a similar approach to that described above for flow. $P_{aw}$ is differentiated ($\Delta P_{aw}/\Delta t$). A positive transient in $\Delta P_{aw}/\Delta t$ of sufficient width, and associated with a threshold increase in $P_{aw}$, would indicate an ineffective effort. In my experience, however, use of flow signal is preferable since changes in $P_{aw}$ associated with ineffective efforts can be quite subtle, particularly when exhalation line resistance is low.

B.2.2.4 Additional Efforts Function (18):

This function detects additional efforts occurring during the inflation phase and is applicable only in pressure-cycled modes (for example, PSV, pressure control). The principles employed are similar to those for ineffective effort detection (16). In pressure-cycled modes, once inspiratory flow reaches its peak value it should progressively decline towards zero. A secondary increase of sufficient duration occurring during the same inflation invariably indicates an additional effort (Giannouli et al, Am. J. Respir. Crit. Care Med. 159: 1716-1725, 1999). This pattern results in a characteristic change in $\Delta$flow/$\Delta$t (FIG. 2). $\Delta$flow/$\Delta$t is negative early in the inflation phase, beyond peak flow, as expected. However, instead of remaining negative until the end of the phase, it becomes positive (point "c", FIG. 2) for a while before becoming negative again point "d", FIG. 2). In the preferred embodiment, additional efforts are identified if there are positive transients in $\Delta$flow/$\Delta$t between the time of peak inspiratory flow and $T_{off}$. To eliminate artifactual positive transients related to non-specific noise, two additional optional requirements are specified: a) Flow at the end of the positive $\Delta$flow/$\Delta$t transient (point "d", FIG. 2) should be higher than flow at the onset of the transient (point "c", FIG. 2) by a specified amount. In the illustrated example it was higher by 0.2 l/second. A minimum required value of 0.05 l/sec is suggested. b) The difference between instantaneous flow beyond point "c" and flow at point "c" is integrated between point "c" and $T_{off}$ (shaded area). The integral should exceed a specified value. A value of 0.03 l is suggested. When an additional effort is identified its time is stored in memory. From this, the number of additional efforts per minute can be calculated and displayed (19).

B.2.2.5 Patient Rate/$T_{TOT}$ Function (20):

This function simply adds all events identified as $T_{on}$ (by the IRQ process (12)), ineffective efforts (identified by ineffective efforts function (16)) and additional efforts (identified by additional efforts function (18)) stored in memory over a specified period. The specified period may be 1.0 minute, or any other interval selected by manufacturer or user. A preferred approach (20) is to count all events identified over an interval corresponding to a specified number of ventilator cycles (e.g. 10 ventilator cycles). From this, average patient rate is calculated from [(number of events*60)/(period covered by specified number of ventilator cycles)]. Patient $T_{TOT}$ is then calculated from [60/patient rate]. Patient rate and average $T_{TOT}$ values are updated at suitable intervals, preferably after each elapsed ventilator cycle. Patient rate and/or average patient $T_{TOT}$ may be displayed (21).

At times in the assist/control modes the patient is apneic, there being no respiratory efforts, effective or not. Likewise, at times in the pressure support mode, the patient develops recurrent periods of central apnea during which there are no efforts. Inclusion of these apneic periods in the calculation of average patient rate/$T_{TOT}$ would result in substantial underestimation in the respiratory rate of the patient when he/she is making respiratory efforts. By extension, this error would result in overestimation of patient $T_{TOT}$ when patient is making respiratory efforts. A number of approaches can be implemented to avoid this error. For example, periods in excess of a specified duration (for example, 10 seconds) during which there were no efforts of any kind (i.e. effective, ineffective or additional) are excluded from analysis. In another approach, the intervals between successive efforts (whether they triggered the ventilator (as indicated by $T_{on}$), were ineffective or additional) are tabulated. Intervals exceeding the normal variance of this variable (for example, >mean+2 standard deviations) are excluded from analysis of patient respiratory rate/ $T_{TOT}$.

B.2.3 Functions to Calculate Ventilator $T_I$ Error:

B.2.3.1 Desirable $T_I$ Function (22):

This calculates the ventilator inflation phase duration that would result in a physiologically desirable $T_I/T_{TOT}$. Desirable $T_I$ is estimated from patient current average $T_{TOT}$ value (20) and the desirable $T_I/T_{TOT}$ ratio, with the latter being either a user selected value (11) or a default value (see A.5). Because patient current average $T_{TOT}$ value (20) is updated continuously at suitable intervals, desirable $T_I$ is automatically updated at the same intervals, preferably after each elapsed ventilator cycle. Desirable $T_I$ is communicated to the ventilator (23) for use to adjust ventilator $T_I$ or for display to the user. It is recommended that a minimum (e.g. 0.5 second) and a maximum (e.g. 2.5 second) be assigned to this value.

B.2.3.2 Actual $T_I$ Function (24):

This calculates the average duration of inflation phase of a suitable number of elapsed ventilator cycles. Ventilator $T_I$ is calculated for each elapsed breath from the difference between $T_{on}$ and $T_{off}$ of that breath. Results of individual breaths are stored in a buffer. Actual $T_I$ is the average of such values over a suitable number of elapsed breaths. This number should ideally be the same as the number used to estimate average patient $T_{TOT}$ (20). In the preferred embodiment, the number is 10 breaths. Actual $T_I$ is updated at suitable intervals, preferably after each elapsed ventilator cycle.

B.2.3.3 $T_I$ Error Function (25):

This function calculates the average difference between actual (24) and desirable (22) $T_I$. An alternate format is to calculate the difference between actual and desired $T_I/T_{TOT}$ with the former calculated from actual $T_I$ (24)/patient $T_{TOT}$ (20). $T_I$ error is updated at suitable intervals, preferably after each elapsed ventilator cycle. $T_I$ error is communicated to the ventilator (26) for use to adjust ventilator $T_I$ or for display to the user.

B.2.4 Functions for the Control of Ventilator Cycling-Off Time:

There are a number of ways by which the output of the aforementioned functions can be used to continuously adjust ventilator cycling in order to obtain a desirable $T_I/T_{TOT}$. The choice would clearly be up to the ventilator manufacturer. Only a few examples of possible approaches are discussed here.

In the assist/control modes, the desirable $T_I$ output (23) can be used to continuously update the programmed ventilator cycle duration (ventilator $T_I$) in the ventilator's control circuitry. In this fashion, ventilator $T_I$ changes continuously and appropriately in response to spontaneous changes in patient rate, which are quite frequent. Because in the volume cycled mode tidal volume is directly related to ventilator $T_I$, changes in the latter induced by the current invention will necessarily result in similar changes in delivered tidal volume. This may be desirable in some cases in that an increase in patient rate, with a consequent reduction in ventilator $T_I$, would result in a reduction in tidal volume, maintaining ventilation approximately the same and avoiding over-ventilation. Some users, however, may prefer to partially or completely avoid changes in tidal volume in response to changes in respiratory rate. In this case, an option may be provided whereby a decrease in ventilator $T_I$ is automatically offset by appropriate and simultaneous increase in flow rate, and vice versa. The adjustment in flow rate can be designed to completely or only partially offset the change in tidal volume resulting from the change in ventilator $T_I$. For example, the simultaneous % change in flow rate can be set to be a fraction of the % change in ventilator $T_I$ with said fraction being user-specified or a default value (for example, 50%, 60% etc).

Frequently, the duration of patient inspiratory effort varies from breath to breath. In this case, the use of a ventilator $T_I$, corresponding to an estimated average patient $T_I$, may result in the ventilator cycling off before the end of inspiratory effort in some breaths. In another aspect of this invention, the implemented ventilator $T_I$ corresponds to the desirable $T_I$ generated by the current invention (23) plus a specified amount (for example, 0.2 sec) or specified fraction (for example, 10% etc). In this fashion, the frequency of cycles in which the ventilator inflation phase terminates before patient effort is reduced. The increase, over desirable $T_I$, to be implemented may be a user input or a default value. It is readily possible to identify cycles in which the ventilator breath terminated prematurely from observing the flow pattern on the ventilator screen. The adjustable incremental amount to be used can, accordingly, be set by the user to minimize the occurrence of such events.

The same approach can be used to cycle off the ventilator in the pressure support mode. Thus, instead of the conventional flow-based cycling-off mechanism, the ventilator can be made to cycle off at the desirable $T_I$ identified by the present invention (23). An option to alter the pressure level simultaneously, as desirable $T_I$ changes, may also be provided to partially or completely offset the changes in tidal volume resulting from the different $T_I$. Additionally, an option to increase the desirable $T_I$ (23) by a specified amount or percent (as in the case of volume cycled ventilation described above) before implementation can be provided to minimize instances of ventilator cycle terminating before patient effort.

An alternative and preferred approach, however, is to retain the flow-based cycling-off mechanism and utilize the results of the current invention to continuously adjust the flow threshold for cycling off. By retaining the flow-based cycling-off mechanism, spontaneous changes in duration of patient inspiratory effort continue to influence ventilator $T_I$, since a longer patient $T_I$ will delay the point at which the flow threshold is reached, and vice versa. However, the present invention can provide the flow threshold that will result in a desirable $T_I/T_{TOT}$.

There are several approaches by which the results of the current invention can be used to continuously adjust the cycling-off flow threshold in order to obtain a desirable $T_I/T_{TOT}$ ratio (closed loop control of flow threshold). Four such functions are described here. All functions utilize the $T_I$ error signal (26) to effect changes in flow threshold. The ventilator manufacturer may select one of them or utilize some other control paradigm of his choice. It is recognized that because of the spontaneous breath-by-breath differences in patient $T_{TOT}$ and $T_I$, feedback should not operate on a breath-by-breath basis. Rather, the average error calculated over a number of elapsed breaths should be used, as done here (25). Furthermore, because it is not clinically critical to rapidly adjust the flow threshold, feedback with slow response is preferred to avoid instability.

B.2.4.1 Fixed Change Function (27):

In this approach, a fixed increment or decrement in flow threshold is implemented depending on magnitude and polarity of the $T_I$ error signal (25). For example, if $-0.1 < T_I$ error $< 0.1$, no change is implemented. If $T_I$ error $> 0.1$ second, flow threshold is increased by a fixed amount and if it is $<-0.1$ second, threshold is decreased by a fixed amount. A value of 0.05 l/second is used in the illustrated embodiment (27) but other values can obviously be used. The larger the step change, the faster the response but the more likely it is for the system to overcorrect and have an oscillatory response. Because the full effect of the implemented change on $T_I$ error will not become apparent until a number of breaths have elapsed (since the $T_I$ error (25) is based on average of a number of breaths) step changes in flow threshold are computed only every "n" breaths, where "n" is the number of breaths used in calculating $T_I$ error (25) (see Main Program Loop Function (33). In the preferred embodiment, I have used n=10 (33).

B.2.4.2 Custom Change Function (28):

Here the recommended change in flow threshold is based on the average rate of change in flow in the terminal part of the inflation phase in a suitable number of elapsed breaths. To determine the flow VS time slope, flow at $T_{off}$ and at a suitable interval before $T_{off}$ is measured in a suitable number of elapsed breaths. The difference between average flow at the two points divided by the interval between the two points of measurement provides the relevant slope. In the preferred embodiment (28), I have used an interval of 0.2 second and 10 elapsed breaths. The recommended change in flow threshold is then calculated from $T_I$ error*calculated slope. Because the flow VS time relation in pressure support ventilation is usually not linear, the calculated slope over an arbitrarily selected interval may not be representative of the slope before or after this interval. For this reason, it is prudent not to apply the recommended change (from $T_I$ error*calculated slope) all at once. In the preferred embodiment (28), the recommended change is multiplied by an attenuation factor (e.g. 0.5). This will slow the correction somewhat but will improve stability. Other attenuation factors may be used depending on manufacturer preference. An alternative approach (not illustrated) is to fit the flow VS time relation in elapsed breaths with a non-linear function and calculate the required change in flow threshold from $T_I$ error (25) and said non-linear function.

As in the case of the fixed change function (27), because the full effect of the implemented change on $T_I$ error will not become apparent until a number of breaths have elapsed (since the $T_I$ error (25) is based on average of a number of breaths) custom changes in flow threshold are computed only every "n" breaths where "n" is the number of breaths used in calculating $T_I$ error (25). (see Main Program Loop Function (33).

B.2.4.3 Hybrid Change Function (29):

Although the custom change function (28) should, on average, result in faster correction than the fixed change function (27), at times flow is quite flat over short intervals near the end of the inflation phase. In this case, the custom function (28) would result in very small recommended changes. In the hybrid function, the changes recommended by both the fixed (27) and custom (28) functions are calculated and the one with the higher absolute value is used. The hybrid function is executed at the same time the other two functions are executed (i.e. every "n" breaths). The hybrid function is preferred for general use and its output is the one utilized in the preferred embodiment (see Timed IRQ process (12)). However, the result of the fixed (27) or custom (28) functions may be the preferred output under some circumstances.

Based on manufacturer preference, the recommended change in flow threshold, as derived from any of the above three functions (27-29), can be outputted (30) in l/second or as % peak inspiratory flow. For the sake of the latter expression, the recommended change is divided by peak inspiratory flow obtained from the peak inspiratory flow function (14). The recommended change can then be added to or subtracted from the flow threshold value currently stored in the ventilator's control system. Alternatively, the recommended change can be added to the average value of flow at $T_{off}$ (obtained from the custom change function (28)), which is an approximation of the current flow threshold, and the result is expressed (30) as recommended flow threshold, as opposed to recommended change in flow threshold. This, again, can be expressed either in l/second or as % peak flow according to manufacturer preference.

B.2.4.4 Proportional/Integral/Derivative (PID) Function (31):

Here, rather than computing a recommended change in flow threshold, as done by the above three functions (27 to 29), flow threshold is directly controlled by the $T_I$ error function (25) using the standard PID approach. A composite error signal with three components is generated (31) from the $T_I$ error signal (26). One component is proportional to $T_I$ error (26), the other is proportional to the integral of $T_I$ error (26) and the third is proportional to the derivative of $T_I$ error (26). The gains of the individual components are adjusted for optimal performance. This composite error signal (32) is then used for ongoing adjustment of flow threshold for cycling off.

With all methods described above for closed-loop control of flow threshold (27,28,29,31) it is recommended that the ventilator manufacturer place a limit on how low the flow threshold for cycling off can go. This will prevent instances of cycling off being prevented because of positive offsets in the ventilator's flow signal. The magnitude of this set minimum value will clearly depend on the quality of the ventilator's flow signal (i.e. tendency to drift . . . etc).

B.2.5 Main Program Loop Function (33):

This function is initiated with every $T_{off}$. It then executes the various functions in the appropriate order at a fixed point in the breath cycle to guarantee the availability of all necessary variables.

Detailed flowcharts of the various functions used in the preferred embodiment are shown in FIGS. 4 to 13.

SUMMARY OF DISCLOSURE

In summary of this disclosure, the present invention provides method and apparatus for automatic ongoing adjustment of the cycling-off time of ventilator inflation phase during assisted ventilation in accordance with true respiratory rate of the patient. Modifications are possible within the scope of this invention.

The invention claimed is:

1. A method for automatic ongoing adjustment of the cycling-off time of ventilator inflation phase during assisted ventilation in accordance with true respiratory rate of a patient, comprising:
   generating electrical signal(s) corresponding to rate of gas flow exchanged between patient and ventilator (flow) and/or to airway pressure ($P_{aw}$);
   determining true respiratory rate of patient (patient RR) on an ongoing basis from said flow and/or $P_{aw}$ signals;
   estimating current average cycle duration of patient respiratory efforts (current patient $T_{TOT}$) from said patient RR;
   calculating a current desirable duration of the inhalation phase (desirable $T_I$) from the product of current patient $T_{TOT}$ and a $T_I/T_{TOT}$ ratio chosen to be in a physiological range; and
   causing ventilator inflation phase to terminate in accordance with said desirable $T_I$.

2. The method of claim 1 wherein ongoing patient RR is estimated from the sum of patient-triggered ventilator cycles, ineffective efforts during exhalation and additional efforts during the ventilator's inflation phase.

3. The method of claim 2 wherein ineffective efforts are estimated from the derivative of the flow signal ($\Delta$flow/$\Delta$t), and identifying negative transients in said signal that meet specified duration criteria, and/or from the derivative of the $P_{aw}$ signal ($\Delta P_{aw}/\Delta t$) and identifying positive transients in said signal that meet specified duration criteria.

4. The method of claim 1 wherein ongoing patient RR is determined from a composite signal incorporating both flow and $P_{aw}$.

5. The method of claim 1 wherein ongoing patient RR is determined by spectral analysis of the flow and/or $P_{aw}$ signal.

6. The method of claim 1 wherein ongoing patient RR is determined from electrical inductance or impedance of the chest wall, strain gauges placed on chest wall, or from signals measuring electrical activity of respiratory muscles.

7. The method of claim 1 wherein periods of central apnea are excluded when estimating patient RR and patient $T_{TOT}$.

8. The method of claim 1 wherein a minimum and/or maximum limit is placed on the calculated desirable $T_I$.

9. The method of claim 1 wherein the $T_I/T_{TOT}$ ratio to be used in calculating desirable $T_I$ is a user input.

10. The method of claim 1 wherein the $T_I/T_{TOT}$ ratio to be used in calculating desirable $T_I$ is a default value or a default function of patient RR.

11. The method of claim 1 wherein calculated desirable $T_I$ is used to directly determine the duration of the inflation phase of the ventilator (ventilator $T_I$).

12. The method of claim 11 wherein ventilator $T_I$ is set to equal desirable $T_I$ plus a specified amount or a specified percent.

13. The method of claim 1 wherein actual $T_I$ is also determined in a number of recently elapsed breaths from the difference between cycling off time and either trigger time or time of onset of inspiratory effort, and a $T_I$ error signal corresponding to the difference between actual and desirable $T_I$ is generated.

14. The method of claim 13 wherein said $T_I$ error signal is used to adjust the flow threshold for cycling off in the pressure support mode.

15. The method of claim 14 wherein adjustment of flow threshold is effected by fixed step increases or decreases in said threshold with polarity of said step changes being determined by polarity of the $T_I$ error signal.

16. The method of claim 14 wherein adjustment of flow threshold is effected by variable step increases or decreases in said threshold with magnitude of said variable step changes being determined by magnitude of $T_I$ error signal and the estimated rate of change in flow in the terminal part of the ventilators inflation phase.

17. The method of claim 14 wherein flow threshold for cycling off is adjusted based on the magnitude of a composite signal consisting of the $T_I$ error signal and/or the integral of the $T_I$ error signal and/or the derivative of the $T_I$ error signal.

18. The methods of any one of claims 1-16 or 17 wherein changes in ventilator $T_I$ resulting from application of said methods are automatically accompanied by changes in the delivered flow rate (in volume-cycled ventilation) or in delivered pressure support (in pressure support ventilation) intended to partially or completely offset the expected change in delivered tidal volume.

19. The method of claim 1 wherein the physiological range is from 0.25 to 0.50.

20. A device for automatic ongoing adjustment of the cycling-off time of ventilator inflation phase during assisted ventilation in accordance with true respiratory rate of the patient, comprising:
circuitry for generating electrical signal(s) corresponding to the flow exchanged between patient and ventilator (flow) and/or to airway pressure ($P_{aw}$);
digital or analog circuitry means for determining true respiratory rate of patient (patient RR) on an ongoing basis from said flow and/or $P_{aw}$ signals;
digital or analog circuitry means for estimating current average cycle duration of patient respiratory efforts (current patient $T_{TOT}$) from said patient RR;
digital or analog circuitry means for calculating a current desirable duration of the inhalation phase (desirable $T_I$) from the product of current patient $T_{TOT}$ and a $T_I/T_{TOT}$ ratio chosen to be in a physiological range; and
means to cycle off ventilator inflation phase in accordance with said desirable $T_I$.

21. The device of claim 20 wherein ongoing patient RR is estimated from the sum of patient-triggered ventilator cycles, ineffective efforts during exhalation and additional efforts during the ventilator's inflation phase.

22. The device of claim 21 wherein ineffective efforts are estimated from the derivative of the flow signal ($\Delta$flow/$\Delta$t), and identifying negative transients in said signal that meet specified duration criteria, and/or from the derivative of the $P_{aw}$ signal ($\Delta P_{aw}/\Delta t$) and identifying positive transients in said signal that meet specified duration criteria.

23. The device of claim 20 wherein ongoing patient RR is determined from a composite signal incorporating both flow and $P_{aw}$ signals.

24. The device of claim 20 wherein ongoing patient RR is determined by spectral analysis of the flow and/or $P_{aw}$ signal.

25. The device of claim 20 wherein ongoing patient RR is determined from electrical inductance or impedance of the chest wall, strain gauges placed on chest wall, or from signals measuring electrical activity of respiratory muscles.

26. The device of claim 20 wherein periods of central apnea are excluded when estimating patient RR and patient $T_{TOT}$.

27. The device of claim 20 wherein a minimum and/or maximum limit is placed on the calculated desirable $T_I$.

28. The device of claim 20 wherein the $T_I/T_{TOT}$ ratio to be used in calculating desirable $T_I$ is a user input.

29. The device of claim 20 wherein the $T_I/T_{TOT}$ ratio to be used in calculating desirable $T_I$ is a default value or a default function of patient RR.

30. The device of claim 20 wherein calculated desirable $T_I$ is used to directly determine the duration of the inflation phase of the ventilator (ventilator $T_I$).

31. The device of claim 30 wherein ventilator $T_I$ is set to equal desirable $T_I$ plus a specified amount or a specified percent.

32. The device of claim 20 wherein actual $T_I$ is also determined in a number of recently elapsed breaths from the difference between cycling off time and either trigger time or time of onset of inspiratory effort, and a $T_I$ error signal corresponding to the difference between actual and desirable $T_I$ is generated.

33. The device of claim 32 wherein said $T_I$ error signal is used to adjust the flow threshold for cycling off in the pressure support mode.

34. The device of claim 33 wherein adjustment of flow threshold is effected by fixed step increases or decreases in said threshold with polarity of said step changes being determined by polarity of the $T_I$ error signal.

35. The device of claim 33 wherein adjustment of flow threshold is effected by variable step increases or decreases in said threshold with magnitude of said variable step changes being determined by magnitude of $T_I$ error signal and the estimated rate of change in flow in the terminal part of the ventilator's inflation phase.

36. The device of claim 33 wherein flow threshold for cycling off is adjusted based on the magnitude of a composite signal consisting of the $T_I$ error signal and/or the integral of the $T_I$ error signal and/or the derivative of the $T_I$ error signal.

37. The devices of any one of claims 20-35 or 36 wherein changes in ventilator $T_I$ resulting from application of said methods are automatically accompanied by changes in the delivered flow rate (in volume-cycled ventilation) or in delivered pressure support (in pressure support ventilation) intended to partially or completely offset the expected change in delivered tidal volume.

38. The devices of any one of claims 20-35 or 36 wherein values of any or all of ineffective efforts, additional efforts, patient RR, desirable $T_I$, $T_I$ error, and/or recommended flow threshold for cycling off, or recommended change thereof, are displayed to the user.

39. The device of claim 20 wherein the physiological range is from 0.25 to 0.50.

* * * * *